Figure 1:
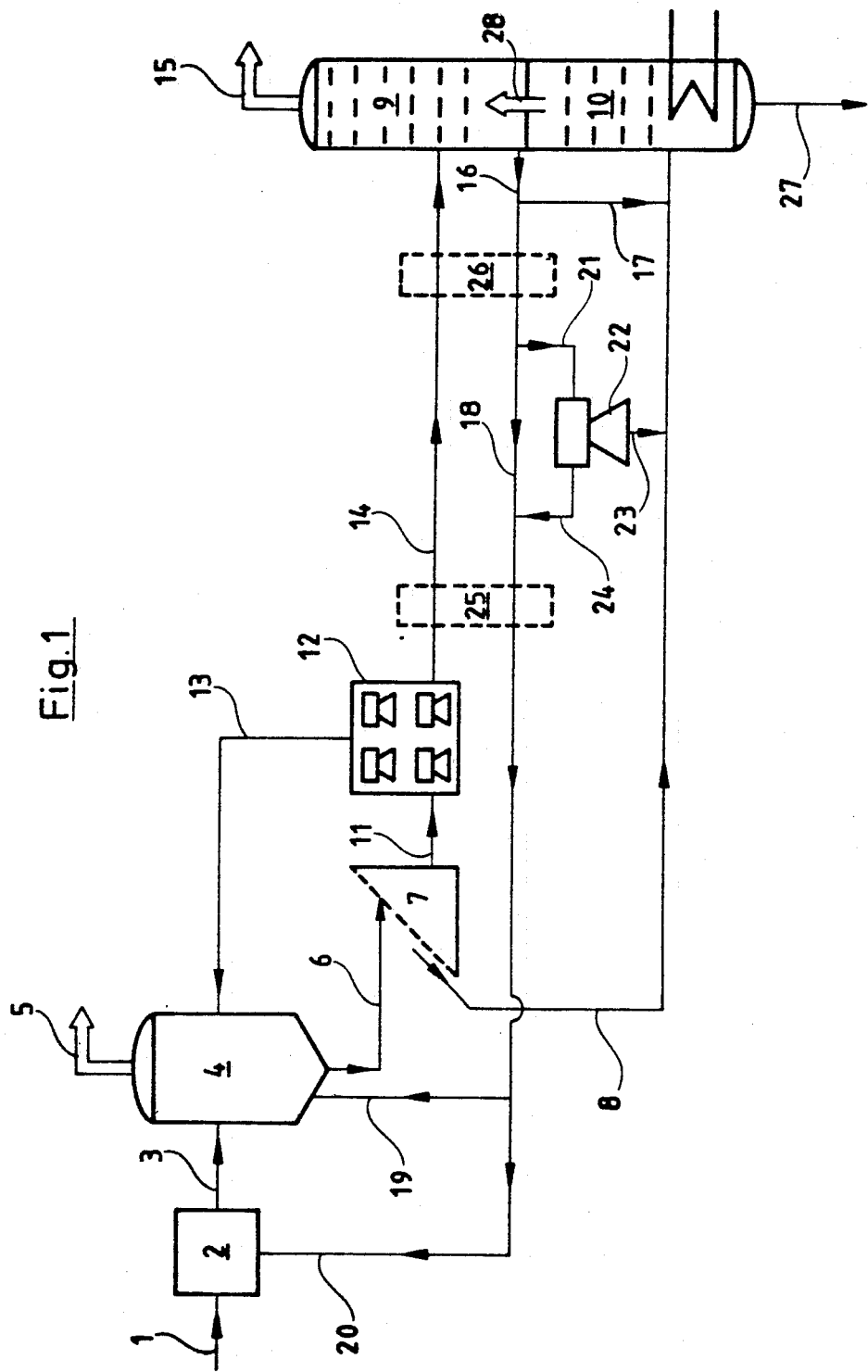

United States Patent [19]

Granstedt

[11] Patent Number: 4,952,503
[45] Date of Patent: Aug. 28, 1990

[54] PROCESS FOR THE PRODUCTION OF ETHANOL

[76] Inventor: Jürgen Granstedt, Vitalisvägen 11, S-112 55 Stockholm, Sweden

[21] Appl. No.: 882,924
[22] PCT Filed: Nov. 28, 1985
[86] PCT. No.: PCT/SE85/00493
 § 371 Date: Jun. 19, 1986
 § 102(e) Date: Jun. 19, 1986
[87] PCT Pub. No.: WO86/03514
 PCT Pub. Date: Jun. 19, 1986

[30] Foreign Application Priority Data

Dec. 7, 1984 [SE] Sweden .................. 8406215

[51] Int. Cl.$^5$ .............................. C17P 7/06
[52] U.S. Cl. ...................... 435/161; 203/19; 426/7; 426/11; 426/13; 426/14; 435/162; 435/165; 435/813
[58] Field of Search ............ 435/161, 162, 165, 813; 203/19; 426/7, 11, 13, 14

[56] References Cited

U.S. PATENT DOCUMENTS

| | | | |
|---|---|---|---|
| 4,361,651 | 11/1982 | Keim | 435/161 |
| 4,376,163 | 3/1983 | Ehnstrom | 435/161 |
| 4,460,687 | 7/1984 | Ehnstrom | 435/161 |
| 4,497,896 | 2/1985 | Assarsson et al. | 435/165 |
| 4,522,920 | 6/1985 | Thorsson et al. | 435/161 |
| 4,617,270 | 10/1986 | Anderson et al. | 435/161 |

FOREIGN PATENT DOCUMENTS

WO83/01627 11/1982 PCT Int'l Appl.

*Primary Examiner*—Robert J. Warden
*Assistant Examiner*—Timothy M. McMahon
*Attorney, Agent, or Firm*—Davis Hoxie Faithfull & Hapgood

[57] ABSTRACT

In the production of ethanol by continuous fermentation in a fermentor (4) with continuous stillage recirculation (19, 20) to the fermentor, the fermentation liquid (6) continuously withdrawn from the fermentor is first sieved in a straining step (7) for separation of coarse solid particles. Then the fermentation liquid (11) is separated in a yeast separation step (12), from which a yeast stream (13) is recirculated to the fermentor (4) and a yeast-free stream (14) is fed to a primary distillation step (9). From the bottom stream (16) from the distillation step (9) a part (19, 20) is recirculated to the fermentor and another part is subjected to final stripping in a secondary distillation step (10). By installing a further centrifugal separation step (22) in the stream (14), which is fed to the distillation step (9), or in the bottom stream (16) which leaves the distillation step (9), finer inert solid particles can be removed from the circulation circuit comprising the distillation step (9) and the fermentor (4). Thereby a considerable saving of separator capacity in the yeast separation step (12) and an improved fluidity in the system can be achieved.

2 Claims, 2 Drawing Sheets

PROCESS FOR THE PRODUCTION OF ETHANOL

The present invention relates to a process for the production of ethanol by continuous fermentation of a carbon hydrate containing substrate in a fermentor, in which process a stream of fermentation liquor is continuously withdrawn from the fermentor and divided in a centrifugal separation step into a yeast enriched stream, which is recirculated to the fermentor, and into an essentially yeast-free stream, which is divided in a primary distillation step into a top stream enriched in ethanol and a remaining liquid bottom stream, of which a part is recirculated to the fermentor and the remaining part is fed to a secondary distillation step for division into a vapour stream containing the remaining ethanol and an ethanol impoverished stillage stream.

In a known continuous ethanol fermentation process of the kind introductively mentioned, such as disclosed in applicant's international application WO No. 83/01627, coarse solid particles are first separated in a straining step from the fermentation liquor continuously withdrawn from the fermentor, whereafter the stream that passes through the sieves is fed to a centrifugal separation step for separation into a yeast phase, which is recirculated to the fermentor, and a phase freed from yeast, which is fed to a primary distillation step in a distillation plant. Part of the solid, non-fermentable or inert material continuously fed to the process with the raw material is discharged from the process circuit in the form of coarse particles, which as sieve rejects is discharged from the circulation loop, which comprises the fermentor and the primary distillation step. The remaining part of inert solid material that continuously must be removed, is discharged with that part of the bottom stream from the primary distillation step which is fed to a secondary distillation step, also called stripping step, in which the remaining ethanol is stripped off and the liquid stream is concentrated to a final stillage stream. As a consequence thereof, the part of the solid inert material which cannot be screened off with the sieves must, at steady-state condition, reach a certain concentration in the bottom stream from the primary distillation step to be discharged in the correct amount from the process circuit through the stillage stream from the stripper.

In certain cases, such as in fermentation on grain raw material, a considerable concentration of fine particles arises in the streams to and from the primary distillation step, for example in the range of 4–6% by weight. Moreover, it can be foreseen that a still higher concentration of these "fines" must be built up in the fermentor-yeast separator-circuit, since the inert particles further tend to be enriched in the yeast phase, which is recirculated from the periphery of the yeast separators to the fermentor. Since further the proportion in the fermentation liquor from the fermentor normally amounts to no more than 2% by weight DS (dry solids), the sludge capacity of the yeast separators will to a large part be occupied by the inert material. As a consequence, the very large part of the flow fed to the yeast separator, at grain fermentation in the range of 60–70%, must be recirculated as sludge phase to the fermentor. Therefore large separator capacity is acquired, since the amount of sludge in this case is the dimensioning factor.

One way to reduce the need for yeast separator capacity is to change the flow rate between effluent and sludge phase, that is to increase the effluent flow and decrease the sludge, flow. Thereby the required concentration of inert solid material in the stream to and from the primary distillation step could be achieved simultaneously as a lower steady-state concentration of solid inert material in the fermentor-yeast separator circuit would be required, which could make possible a reduction in yeast separator capacity. However, the disadvantage of such a modification is increased yeast losses, which arise due to increased yeast drainage with the effluent to the primary distillation step, in which alive yeast is killed off.

The object of the present invention is to reduce the concentration of solid inert material in the fermentor-yeast separator circuit and to reduce the required yeast separator capacity while maintaining the yeast losses at an unchanged low level.

This object is reached according to the invention in a process of the kind introductively mentioned by dividing in a further centrifugal separation step at least a part of the liquid stream fed to the primary distillation step or the liquid stream discharge from the primary distillation step into a stream impoverished in fine particles and a sludge stream enriched in fine particles and discharging said sludge stream from the circulation circuit, which comprises the primary distillation step and the fermentor.

According to a preferred embodiment of the invention, the further centrifugal separation step is located after the primary distillation step. Thereby, at least two advantages are reached compared with the case of locating the centrifugal separator before the primary distillation step. One advantage resides in the fact that the separated sludge concentrate is comparatively impoverished in ethanol and can be fed directly to the secondary distillation step for final stripping together with the sieve rejects and possible remaining liquid stream from the primary distillation step. A second advantage is that some part nonseparable protein in solved or colloidal state in the feed streem to the primary distillation step is transferred into separable form through coagulation due to heating during heat exchange with the recirculation stream from the primary distillation step and further during heating in the distillation step itself. These protein aggregates thus formed can now be separated off directly and do not have to be recirculated to the fermentor.

In the case a further centrifugal separation step is located before the primary distillation step, it is obtained in the separated sludge phase an ethanol concentration of about the same magnitude as that of flow fed to the primary distillation step, that is normally in the range of 4–6% by weight. If the separation conditions are selected so that the concentration of solid material in the sludge phase from the separation step is high and the total sludge stream therefore can be kept relatively small, a sludge phase can be fed directly to the stripping step despite its high ethanol concentration without significantly impairing the ethanol yield. If the sludge phase is comparatively large, that is if it comprises a significant part of the liquid to be stripped to final stillage, a feasible way to avoid impaired ethanol yield is to strip off most of the ethanol in the sludge phase in a separate smaller column. The bottom flow from this column can then suitably be fed to a stripping step also used for stripping sieve rejects and the possible further part of the bottom stream from the primary distillation step.

The further centrifugal separation step according to the invention makes possible a considerable reduction of solid DS in the circulation circuit comprising fermentor, yeast separator and primary distillation step. The most conspicuous effect thereof is that the flow ratio between effluent and sludge phase from the yeast losses, which, at unchanged ethanol production, makes possible a considerable reduction of the sludge flow recirculated to the fermentor as well as of the feed flow to the yeast separators. If for example the amount of inert DS to the yeast separators is reduced from e.g. 8% by weight to 3% by weight by installing a centrifugal separator according to the invention, the required yeast separator capacity can be reduced to about half, which means a considerably reduced investment and energy costs, since the required further separator capacity is far lower than saved yeast separator capacity.

The possibility of maintaining a lower concentration of solid inert DS in the circulation circuit due to the invention, provides several further improved process conditions. The fermentation environment in the fermentor is improved, i.e. due to less foaming and facilitated stirring. Less contamination is obtained in the primary mash column and also in further process units such as heat exchangers for heat exchange between the cold yeast-free stream from the yeast separators and recirculation stream from the primary mash column. A lower viscosity of the streams in the circulation circuit improves the fluidity, which facilitates the straining operations and pumping.

Figure 2:
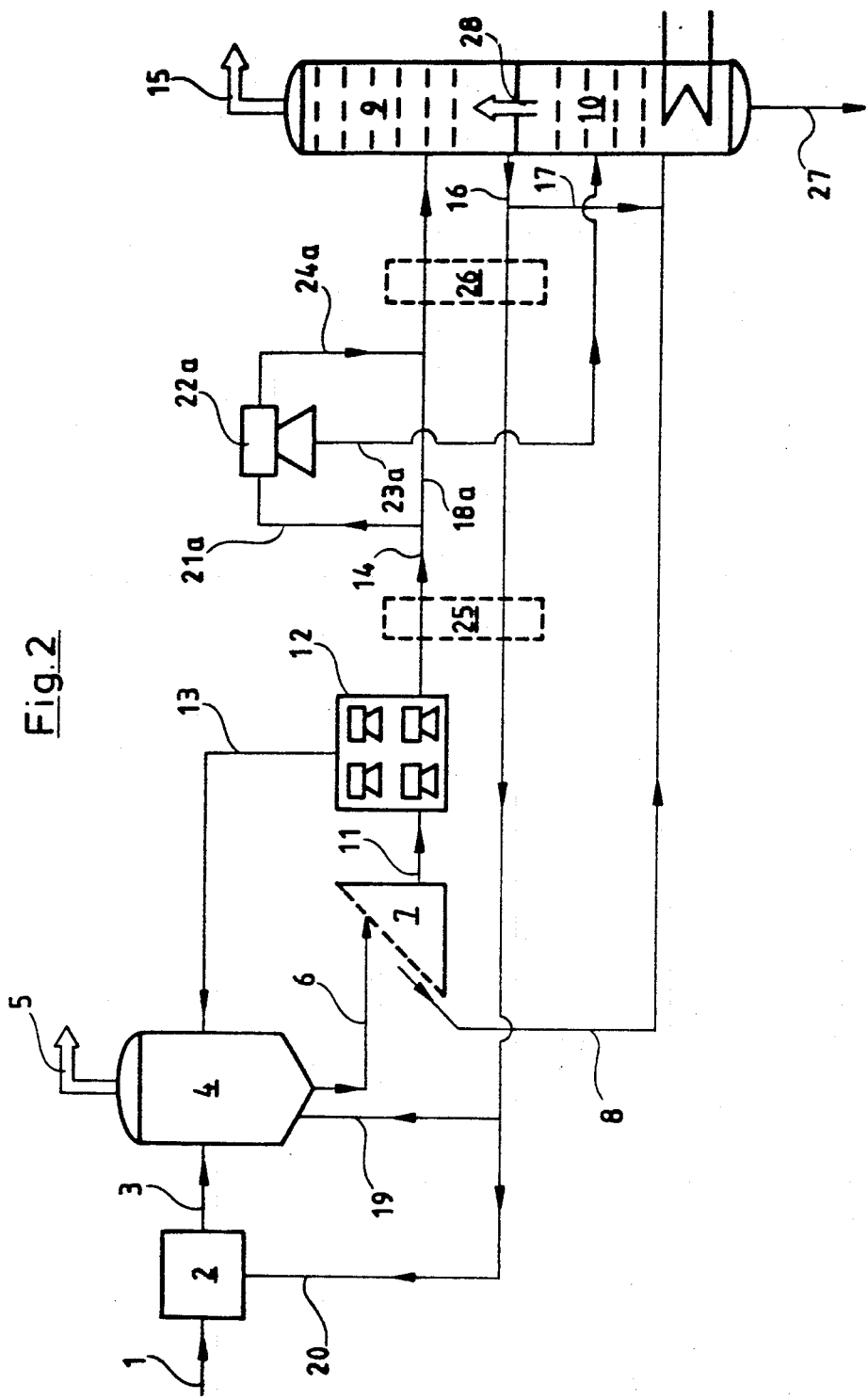

The invention will now be further illustrated by means of a few embodiments of the same, shown as examples, reference being made to the accompanying drawing, in which FIG. 1 shows a flowsheet with an extra separator installed after the primary distillation step, and FIG. 2 shows a flowsheet with an extra separator installed before the primary distillation step.

According to the flowsheet of FIG. 1, fermentation raw material, e.g. milled grain, and required process water are supplied with a stream 1 to a substrate treating step 2, in which enzymatic hydrolysis to fermentable sugars occurs. From the substrate treating step 2 a stream 3 with hydrolysate is fed to a fermentor 4, in which continuous fermentation of the hydrolysate occurs at steady-state conditions by means of yeast suspended in the fermentation liquid during formation of ethanol and carbon dioxide, which is discharged from the top of the fermentor through 5. To maintain constant yeast concentration in the fermentor, air or oxygen is supplied either to the fermentor feed flow 3 or to the fermentor itself to achieve a yeast growth corresponding to minor yeast losses. A stream of fermentation liquor 6 containing ethanol of a concentration in the range of 4–6% by weight is continuously withdrawn from fermentor 4. The stream 6 is fed to a straining step 7 for separating off a sieve reject stream 8, which is withdrawn from the circulation circuit comprising fermentor 4 and a primary distillation 9 and fed to a secondary distillation step 10.

A stream of fermentation liquor 11 freed from coarse particles and fibres is fed to a yeast separation step 12 comprising one or several yeast separators. A heavy phase stream 13 containing essentially all yeast from the stream 11 and also finer inert material not rejected in the straining step 7 is recirculated to fermentor 4. A light phase stream 14 essentially free from yeast is continuously withdrawn from yeast separators 12 and fed to the primary distillation step 9, generally consisting of a multi-stage column. From the top of column 9 the major part of the ethanol present in the yeast-free stream 14 is removed through a vapour stream 15, which normally contains ethanol in the range of 35–40% by weight. A bottom stream 16 having an ethanol concentration in the range of 0.1–0.2% by weight is discharged from the bottom of column 9. In the shown embodiment a partial stream 17 of the bottom stream 16 is sent directly to a stripping column, constituting the secondary distillation step 10. Another partial stream 18 of the bottom stream 16 is recirculated to the fermentor through 19 and/or also to the substrate treating step 2 through 20. A further partial stream 21 of the bottom stream 16 is fed to a further centrifugal separation step 22, in which it is divided into a sludge stream 23 enriched in fine particles and an effluent stream 24. The sludge stream 23 is fed to a stripping column 10, and the effluent stream 24 is recirculated with the stream 18 in the circulation circuit comprising fermentor 4 and the primary distillation step 9.

For heat exchanging the yeast-free stream 14 to be fed to the primary distillation step 9 with the part of the bottom stream 16, which is recirculated to fermentor 4 and/or the substrate treating step 2, a heat exchanger 25 can be installed for heat exchanging the recirculation streams 18 and 24 with the yeast-free stream 14, whereby the inflow to the sludge separator 22 will be warm. Alternatively the heat exchange can be carried out in a heat exchanger 26 installed before the sludge separator 22, whereby the inflow to the same will be cooled down to near fermentor temperature. A warm inflow 21 to the separator 22 can facilitate the separtion, while high temperature operation puts higher demand on the separator functioning from the view of safe operation. Whether heat exchange is to be carried out before or after the separator 22 depends on the type of separator used, and in many cases a division of the heat exchange through one unit 25 and one unit 26 is to be preferred.

If the separation conditions in the centrifugal separation step 22 is selected so that the sludge stream 23 has relatively low sludge concentration, the stream 17 to the stripper 10 can possibly be eliminated. On the contrary, if the sludge stream 23 has a high concentration of inert solid material, the sludge stream 17 will be necessary for balancing the removal of inert material from the circulation circuit and maintaining steady-state.

Likewise depending on the separation conditions in the centrifugal separation step 22, whole or part of the stream recirculated to the fermentor or to the substrate treating step can be passed through the separator 22. In the extreme case the stream 18 can thus be eliminated. Further, an arbitrary part of the recirculation streams 18 and 24 can be used for washing (not shown in FIG. 1) the sieve reject stream 8 from straining step 7 in order to reduce the yeast losses and the ethanol concentration in the sieve reject stream 8.

The sieve reject stream 8 as well as the sludge stream 23 from the centrifugal separation step 22 and the stream 17 are fed to the stripping column 10 for stripping off the remaining ethanol and recovering a concentrated stillage stream 27 from the bottom of the stripping column 10. The ethanol containing vapours 28 from the stripping column 10 are fed to the primary distillation column 9 as direct heating medium. The stripping column 10 and the primary distillation column 9 can suitably be combined in a common column, in which the downwards streaming liquid flow is blocked on an intermediate level for the discharge of the bottom stream 16 from the upper part 9 of the column, which constitutes the primary distillation step.

FIG. 2 shows an embodiment, which is identical with the embodiment shown in FIG. 1 except the location of the sludge separator 22 in the process curcuit. Therefore, the exactly corresponding process units and streams have been given the same figure references as in FIG. 1.

Depending on the selection of sludge separator and separation conditions, whole or part of the yeast free stream 14 from the yeast separation step 12 is fed as feed flow 21a to a further sludge separator 22a. A sludge stream 23a enriched in solid inert material is discharged from the separator 22a and fed to stripping column 10. Since now the sludge stream 23a, contrary to the previous embodiment, has a considerable ethanol concentration being of the same magnitude as that of the inflow 14 to the primary column 9, it can be convenient to add to the stripping column 10 one or a few further distillation trays in comparison with the stripping column of FIG. 1, and to supply the sludge stream 23a on a somewhat higher level to the stripping column 10 than the remaining streams 8 and 17 also fed to the stripping column 10. A stream 24a impoverished in fine particles is sent together with the remaining part 18a of the yeast freestream 14 to the primary column 9.

Of the same reason as mentioned in context with the previous embodiment, one or both of the by-pass streams 17 and 18a can possibly be eliminated depending on the selection of separation conditions and centrifugal separator.

I claim:

1. In a process for the production of ethanol through continuous fermentation of a carbohydrate containing substrate in the presence of yeast in a fermentor, wherein a stream of fermentation liquor is continuously withdrawn from the fermentor, said stream of fermentation liquor is divided in a first centrifugal separation step into a yeast enriched stream, which is recirculated to the fermentor, and an essentially yeast free stream, said yeast free stream is divided in a primary distillation stage into an overhead stream enriched in ethanol and a liquid bottoms stream at least a part of which is recycled to the fermentor, the improvement which comprises straining the stream of fermentation liquor prior to said first centrifugal separation step to separate a stream of coarse particles, centrifuging the yeast free stream prior to said primary distillation stage or centrifuging the liquid bottoms stream directly after removal from the primary distillation stage, to give a stream impoverished in fine particles and a sludge stream enriched in fine particles, blending said stream of coarse particles with the stream enriched in fine particles to form a combined stream, subjecting said combined stream to distillation in a secondary distillation stage, returning a vapor stream from said secondary distillation stage to said primary distillation stage, removing a sludge stream from said secondary distillation stage and discharging the sludge stream from the secondary distillation stage from the circuit which includes the primary distillation stage and the fermentor.

2. In a process for the production of ethanol through continuous fermentation of a carbohydrate containing substrate in the presence of yeast in a fermentor, wherein a stream of fermentation liquor is continuously withdrawn from the fermentor, said stream of fermentation liquor is divided in a first centrifugal separation step into a yeast enriched stream, which is recirculated to the fermentor, and an essentially yeast free stream, said yeast free stream is divided in a primary distillation stage into an overhead stream enriched in ethanol and a liquid bottoms stream at least a part of which is recycled to the fermentor, the improvement which comprises centifuging the liquid bottoms stream directly after removal from the primary distillation stage to give a stream impoverished in fine particles and a sludge stream enriched in fine particles, feeding said sludge stream to a second distillation stage, stripping ethanol and water from said sludge stream in said second distillation stage, to form an ethanol containing stream, charging the ethanol containing stream from said second distillation stage to said first distillation stage and discharging said stripped sludge stream from the circuit which includes the primary distillation stage and the fermentor.

* * * * *

UNITED STATES PATENT AND TRADEMARK OFFICE
CERTIFICATE OF CORRECTION

PATENT NO. : 4,952,503

DATED : August 28, 1990

INVENTOR(S) : Jurgen Granstedt

It is certified that error appears in the above-identified patent and that said Letters Patent is hereby corrected as shown below:

Col. 3, line 6, after "yeast" insert --separation step can be considerably increased without increasing--;

Signed and Sealed this

Seventeenth Day of December, 1991

Attest:

HARRY F. MANBECK, JR.

Attesting Officer

Commissioner of Patents and Trademarks